United States Patent [19]

Lloyd et al.

[11] Patent Number: 4,663,288

[45] Date of Patent: May 5, 1987

[54] PROCESS FOR PURIFICATION OF ENZYMES

[75] Inventors: Norman E. Lloyd, Ridgefield, Conn.; Richard L. Antrim; Richard A. Johnson, both of Clinton, Iowa

[73] Assignee: Nabisco Brands, Inc., Parsippany, N.J.

[21] Appl. No.: 736,921

[22] Filed: May 22, 1985

[51] Int. Cl.$^4$ .............................................. C12N 9/92
[52] U.S. Cl. .................................... 435/234; 435/814
[58] Field of Search ................ 435/234, 814, 815, 816

[56] References Cited

U.S. PATENT DOCUMENTS

| | | | |
|---|---|---|---|
| 3,728,324 | 4/1973 | Borglum | 435/814 X |
| 3,769,168 | 10/1973 | Masuda | 435/201 |
| 3,912,595 | 10/1975 | Philipp et al. | 435/213 |
| 3,972,777 | 8/1976 | Yamada et al. | 435/208 |
| 4,055,469 | 10/1977 | Snoke et al. | 435/183 |
| 4,106,992 | 8/1978 | Vairel et al. | 435/215 |
| 4,144,130 | 3/1979 | Kula et al. | 435/814 X |
| 4,347,322 | 8/1982 | Johnson et al. | 435/179 |

FOREIGN PATENT DOCUMENTS 1004613  2/1977  Canada .............................. 435/814

*Primary Examiner*—Lionel M. Shapiro
*Attorney, Agent, or Firm*—Richard Kornutik

[57] ABSTRACT

The disclosure is directed to the resolubilization of an insoluble glucose isomerase-amine complex, wherein the amine has the general formula:

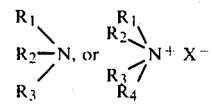

The insoluble enzyme complex may be resolubilized to produce a stable concentrated and purified glucose isomerase preparation by reaction with a resolubilizing mixture comprising a cation exchange resin.

10 Claims, No Drawings

PROCESS FOR PURIFICATION OF ENZYMES

FIELD OF THE INVENTION

This invention relates to the purification of an aqueous glucose isomerase solution and particularly to the treatment of the solution with an amine to form an insoluble complex containing the enzyme and the resolubilization of the glucose isomerase therefrom.

DESCRIPTION OF THE PRIOR ART

Glucose isomerase is an enzyme which converts glucose to fructose. Various microorganisms are known in the art which produce glucose isomerase. For example, microorganisms of the genera Actinoplanes, Aerobacter, Ampullariella, Arthrobacter, Bacillus, Lactobacillus and Streptomyces produce glucose isomerase. Generally glucose isomerase is primarily produced intracellularly and thus the major portion of the glucose isomerase is found within and/or on the cell walls of the microorganisms. Therefore, it is necessary to extract the enzyme from the microbial cells to produce the soluble enzyme. The extraction process results in at least partial disruption of the cell envelope allowing diffusion of the enzyme and other cellular materials into the microbial enzyme extract. Thus, the enzyme extract contains both soluble and insoluble impurities. The insoluble impurities can be easily separated by well known methods, such as by filtration or centrifugation. However, the soluble impurities which are believed to be biological oligomers or polymers, e.g., nucleic acids, non-enzymatic proteins or cell wall components, such as polyuronic acids and the like, are difficult and expensive to remove because they often have chemical or physical properties similar to the desired product.

Methods for removal or separation of undesirable soluble materials from microbial enzyme extracts are well known. A current summary of these methods can be found in Volume XXII of "Methods in Enzymology," pp. 273–287 and pp. 476–556 ( ed. W. E. Jakoby, Academic Press, New York, NY). Various methods for enzyme purification, such as separation based on solubility, separation based on specific affinity and chromatographic separations are described.

Numerous patents also describe various methods for purification of enzymes. U.S. Pat. No. 3,769,168 to Masuda describes the purification of beta-amylase by adsorption, washing and eluting the enzyme with an ionic solution. U.S. Pat. No. 3,912,595 to Philipp et al. describes the purification of a hydrolytic enzyme solution by reversibily complexing the enzyme on a granular support material in a column, after which the enzyme is recovered by elution with a buffer. U.S. Pat. No. 3,972,777 to Yamada et al. describes a method to refine β-galactosidase by selective adsorption on an acid cation exchange resin and then eluting the β-galactosidase from the resin with a buffer. All of these methods encompass contacting an impure enzyme solution with a matrix which will adsorb or bond the enzyme, and then eluting the purified enzyme from the matrix by addition of an ionic solution.

U.S. Pat. No. 4,347,322 to Johnson et al. teaches a chromatographic process for enzyme purification wherein the soluble impurities are preferentially adsorbed by an ion exchange material. In U.S. Pat. No. 4,106,992 to Vairel et al., crude urokinase is subjected to exclusion chromatography utilizing a DEAE-cellulose resin. The described process is principally directed to removing pyrogenic substances from urokinase.

Several patents teach the purification of microbial enzyme extracts by precipitation. U.S. Pat. No. 3,728,244 to Borglum teaches the precipitation of impurities with quaternary ammonium compounds. U.S. Pat. No. 3,794,562 to Bergmeyer et al. teaches the precipitation of impurities using polyethylene-imine. U.S. Pat. No. 4,055,469 to Snoke et al. teaches the precipitation of impurities using synthetic polyelectrolytes. British Pat. No. 1,411,503 to Morisi et al. teaches the precipitation of impurities with a cationic surface active agent. All of these patents teach methods to precipitate and remove impurities while the active enzyme remains in solution.

Quaternary ammonium compounds containing at least one long chain hydrocarbon N-substituent are surface-active electrolytes which can form aggregates or micelles in solution. These compounds are characterized by the hydrophilic quaternary amino group and by the hydrophobic hydrocarbon chain. Many quaternary ammonium compounds have found wide-spread use as antimicrobial agents based on their ability to inactivate or inhibit microorganisms. This property is thought to be a result of the formation of an anion-cation complex between the positively charged quaternary amine and the negatively charged microbial surface.

Quaternary ammonium compounds also form insoluble anion-cation complexes with various negatively charged macromolecules such as proteins. Precipitation, inactivation, denaturation, redispersion and complex formation are all phenomena reported to result from the interaction of proteins with quaternary ammonium compounds.

It was unexpectedly discovered that certain amine compounds may be used in a process to purify glucose isomerase preparations. Such compounds have been described in U.S. patent application Ser. No. 594,188, filed Mar. 28, 1984, the contents of which are incorporated herein by reference.

The tertiary and quaternary amine compounds that can be used in the present method are represented by the following formula:

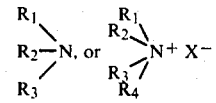

where

R$_1$ is a hydrocarbyl radical containing at least 6 carbon atoms,

R$_2$ is a hydrocarbyl radical containing from about 8 to 20 carbon atoms,

R$_3$ is lower alkyl, and R$_4$ is hydrogen or lower alkyl.

The hydrocarbyl radicals are preferably alkyl, cycloalkyl, alkene, aryl, and aralkyl, and may be substituted by such groups as halide, e.g., chloro and bromo, hydroxy, alkoxy and the like. The hydrocarbyl radicals are also intended to include hydrocarbon chains interrupted by oxygen or sulfur atoms, as in ether or thioether linkages, e.g., diisobutylphenoxyethoxyethyl and diisobutylcresoxyethoxyethyl radicals.

X may be any suitable inorganic or organic anion, such as a halide, nitrate, sulfate, benzenesulfonate, acetate, etc., the anion being inert to the enzyme.

Exemplary of amine groups represented by the above formula which may be used in the process of the invention are dimethylbenzyldodecyl ammonium, stearyldimethylbenzylammonium, distearyldimethylammonium, diethyldioctadecyl ammonium, dimethyldidodecyl ammonium, dimethyldodecylnaphthylmethyl ammonium, dimethylhexadecyldichlorobenzyl ammonium, and dimethyldiisobutylphenoxyethylbenzyl ammonium salts.

Once an insoluble amine-isomerase complex is formed, said complex may be separated from the reaction mixture by normal means such as filtration, centrifugation and the like. After removal of the complex from the crude extract, the isomerase is resolubilized. A useful method as described in U.S. patent application Ser. No. 594,188 involves the addition of an ionized salt solution. Once the enzyme is dissolved, the salt and the amine compound are removed.

It has been surprisingly discovered that if a cation exchange resin is included in the resolubilization mixture, not only is the amine compound effectively transferred to the resin but also the concentration of the ionic salt solution necessary for the resolubilization is dramatically reduced.

BRIEF DESCRIPTION OF THE INVENTION

The present invention provides a method for the resolubilization of an insoluble glucose isomerase-amine complex. The resolubilization is achieved by including in the resolubilizing mixture a cation exchange resin.

The invention provides a method for resolubilizing glucose isomerase from an insoluble glucose isomerase-amine complex comprising reacting said complex in an aqueous medium comprising a cation exchange resin.

DETAILED DESCRIPTION OF THE INVENTION

In accordance with the present invention at least one of the above described amine compounds is added to a glucose isomerase aqueous extract to be purified under conditions such that the amine interacts with the glucose isomerase to form an insoluble isomerase-amine complex which precipitates. The insoluble isomerase-amine complex is then separated by normal means such as filtration, centrifugation or the like. To remove the enzyme from the precipitate, the isomerase-amine complex is added to an ionized salt solution containing a cation exchange resin wherein the complex dissociates and the isomerase resolubilizes. The amine compound is transferred to the resin and may then be separated from the enzyme solution by filtration, or centrifugation to produce a purified, concentrated glucose isomerase preparation having a high specific activity (e.g., activity per mg protein).

The amount of ionized salt and resin required for the re-dissolution of the precipitated enzyme-amine complex can be readily determined by simple test procedures using solutions of varying concentration, i.e., ionic strength, of suitable electrolytes of which sodium chloride is preferred because of economy and availability. A variety of electrolytes can be used as long as they do not adversely affect the glucose isomerase. Usable salts include $Na_2SO_4$, KCl, $K_2SO_4$, $KNO_3$, $NaNO_3$, $NH_4Cl$, $(NH_4)_2SO_4$, magnesium salts, manganese salts, cobalt salts, acetate, citrate, maleate, pyridinium chloride, salts of monovalent anions and cations are preferred. The requisite amount of salt will be determined as the minimum concentration required to dissolve the precipitate. Although sodium chloride does not seem to have any noticeable effect on the enzyme and can be used in concentrated solution to assure complete dissolution of the precipitate, it is preferred to use as low a concentration of salt and still provide efficient resolubilization of the enzyme. This is particularly true if the resolubilized enzyme is to be employed in a immobilized enzyme system such as when adsorbed to DEAE-cellulose.

In fact, as is demonstrated below, a certain amount of resolubilization is achieved even in the absence of salt (i.e., by contacting the precipitate with resin alone). It is possible, therefore, by means of repeated cycles of contacting the precipitate and the resin, to resolubilize the isomerase in the absence of any added salt.

A variety of cation exchange resins may be employed. Useful resins include polystyrene sulfonic acid resins such as Dowex AG 50 W; Duolite C20; Amberlite IR-116, IR-118, IR-120; Amberlite IRN-77; Ionac C-298; Ionac C-249; Zeocarb 225; Diaion SK102, SK103, SK104 SK106; Lewatit PN; Lewatit S-100; Imac C-22, C-12; Kastil C-300; Wofatit KPS-200; Allassion-CS; Kationite KO-2; macroporous polystyrene resins such as Dowex MPC-1; Duolite C-25D, ES-26; Amberlite 200; Imac C-16P; and Lewatit 5-115; phenolic resins such as macroporous Duolite C-3; Kationite K01; Lewatit KSN; Wofatit F; and Zeocarb 215; cationic cellulosic resins such as Cyclase-SE; and dextran resins such as SP Sephadex (sulfopropyl sephadex). These resins may be obtained from the following respective sources.

Allassion—Dia-Prosim, Vitry-sur-Seine, France
Amberlite—Rohm & Haas, Philadelphia
Anionite—Sovient Union
De-Acidite—Permutit Ltd., London
Diaion—Mitsubishi, Tokyo
Duolite—Diamond Shamrock, Redwood City, CA
Imac—Industrieele Naatschappj, Amsterdam
Ionac—Ionac Chem. Co., Birmingham, NJ
Kastel—Montecatini, Milan
Kationite—Soviet Union
Lewatit—Bayer, West Germany
Wofatit—Wofen Dye Factories, East Germany
Zeo-Karb—Permutit Co., London
Dowex—Dow Chemical Co., Midland, MI
Cyclose—Cyclo Chemical, Los Angeles
Sephadex—Pharmacia, Upsala A particularly useful resin is AG50-W-X4 (Bio-Rad Lab., Richmond, Calif.). The amount of resin to be employed can be determined by simple test procedures using varying concentrations of resins.

In some cases, the aqueous enzyme solution from which the enzyme is to be recovered may contain impurities which do form precipitates with the added amine compound prior to precipitating the desired enzyme. In such cases, the addition of amine should be in several stages, usually two stages, in the first of which the impurities are precipitated out and removed before finally precipitating the enzyme in the second stage. The amount of amine needed for the first stage is readily determinable using aliquots of the original enzyme solution to which is added graduated amounts of amine compound. The precipitate formed at each addition is tested for enzyme activity which once detected indicates the amount of precipitant necessary for the first stage precipitation.

In practicing the present invention, it is preferred to use quaternary amines of the above general formula wherein $R_2$ is an alkyl radical containing from about 8 to about 18 carbon atoms, $R_1$ is a radical containing from about 6 to about 10 carbon atoms, $R_3$ and $R_4$ are lower alkyl and X is a halide anion. The more preferred compounds are those wherein $R_2$ is an alkyl radical having from 12 to 18 carbon atoms, $R_1$ is an aralkyl radical having from 7 to 10 carbon atoms, $R_3$ and $R_4$ are lower alkyl radicals and X is a halide radical.

The most preferred compounds may be represented by the following formula:

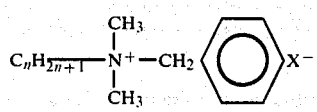

where n is an integer equal to 12, 14, or 16 and X is a halide anion. A product containing these compounds is sold under the name of BTC-835 by Onyx Chemical Co., Jersey City, N.J. BTC-835 is a mixture composed of 50% of a compound where n in the above formula is 14, 40% of a compound where n in the above formula is 12, and 10% of a compound where n in the above formula is 16. Alternatively, a compound sold under the name of Maquat 1412 (50% n-alkyl dimethyl benzyl ammonium chloride, Mason Chemical Co. Chicago, Ill.) is also particularly useful.

The conditions contemplated for performing the instant invention may vary depending on the purity and concentration of the isomerase extract and the particular amine compound utilized. The amount of amine used should be sufficient to precipitate substantially all of the active enzyme and will generally be at least 100 ppm, on a weight per volume basis. The preferred amount is at least about 500 ppm and usually from about 500 ppm to about 5,000 ppm. The most preferred is from about 1,000 to about 3,000 ppm.

The pH should be within the range that is about one pH unit above the isoelectric point (pI) of the enzyme and about one pH unit below the pKa of the amine compound utilized. Preferably, the pH is at a value of from about 5.5 to about 8.5, ideally from about 6.0 to about 8.0 and most preferably from about 7.0 to about 7.4.

The temperature may vary over a wide range from as low as 0° C. up to below the temperature at which heat denaturation or inactivation of the enzyme occurs. For convenience the process will generally be conducted at ambient temperature.

The mechanism of the present process is not completely understood. However, it is believed that the amine interacts with the glucose isomerase to form an insoluble isomerase-amine complex. When the insoluble isomeraseamine complex is added to a highly ionic solution containing a cation exchange resin, the amine is transferred to the resin rendering the isomerase soluble again.

Methods to produce the glucose isomerase extracts used as starting materials in the process of the present invention are well known in the art. For example, an enzyme extract containing glucose isomerase may be obtained by fermentation of microorganisms of a species known to produce glucose isomerase, extracting the enzyme from the mycelia and removing insoluble material by known methods.

The preferred glucose isomerase extracts may be obtained from microorganisms of the genera Actinoplanes, Ampullariella, Aerobacter, Arthrobacter, Bacillus, Micromonospora, Microbispora, Microellobospora, Norcardia, or Streptomyces. Glucose isomerase extract typically may be obtained from microorganisms of the species Streptomyces rubigenosus, Streptomyces olivochromogenes, Bacillus coagulans or Bacillus strearothermophilus.

ANALYTICAL METHODS

Total Protein

Total protein was determined employing a Beckman Model DK-2A Spectrophotometer at a wavelength of 280 millimicrons.

Isomerase Activity-IGIU

IGIU is the abbreviation for International Glucose Isomerase Unit and is that amount of enzyme which will convert 1 micromole of glucose to fructose per minute in a solution initially containing 2 moles of glucose per liter, 0.02 moles of $MgSO_4$ and 0.001 moles of $CoCl_2$ per liter at a pH of 6.84 to 6.85 (0.2M sodium maleate, pH measured at ambient temperature) and at a temperature of 60° C. Glucose isomerase determinations were carried out by the method described by N. E. Lloyd et al., Cereal Chem., 49, No. 5 pp. 544–553 (1972).

The following examples further illustrate the invention.

EXAMPLE I

This example shows the effect of cation exchange resin on the solubilization of the quaternary amine-isomerase complex.

A five-liter of Streptomyces sp. cell-free extract with an isomerase activity of 42.2 IGIU/ml was adjusted to pH 7.2. To this stirred extract was added 10 g of Maquat MC 1412—50% (n-alkyldimethylbenzylammonium chloride, Mason Chemical Company, Chicago, IL) and 25 g Hyflo Supercel (Johns-Mansville, Lompoc, CA). The suspension was stirred 30 minutes and filtered with laboratory vacuum. The filter cake was washed with 200 ml of water and aspirated for about five minutes to remove excess moisture.

The filter cake, 71.46 g, was blended and 10.0 g portions were suspended in salt solutions (150 ml) of various concentrations. After stirring for 20 minutes, aliquots of each suspension were filtered. The filtrates were assayed for soluble isomerase activity. The results were as follows:

| NaCl Conc. Molarity | Soluble Activity | | Recovery % |
|---|---|---|---|
| | IGIU/ml | IGIU Total | |
| 0 | 1.6 | 240 | about 1 |
| 0.05 | 1.3 | 195 | about 1 |
| 0.10 | 1.6 | 240 | about 1 |
| 0.20 | 2.7 | 405 | 1.4 |
| 0.50 | 118.3 | 17,745 | 60.1 |
| 1.00 | 156.2 | 23,430 | 79.4 |

Very little activity was solubilized at salt concentrations below 0.5M.

To determine the effect of cation exchange resin on enzyme solubilization, a 1.5 g (d.b.) portion of AG50-W-X4 resin (Bio-Rad Laboratories, Richmond, CA) (sodium form) was added to each of the original suspensions and stirred for 60 minutes. Samples of each suspension were then centrifuged, and the supernates were analyzed for soluble isomerase activity. The results were as follows:

| NaCl Conc. | Resin Wt. | Soluble Activity | | Recovery % |
|---|---|---|---|---|
| (Molarity) | (Grams) | IGIU/ml | IGIU Total | |
| 0 | 1.5 | 55.5 | 8,295 | 28.1 |
| 0.05 | 1.5 | 157.4 | 23,610 | 80.0 |
| 0.10 | 1.5 | 146.5 | 21,973 | 74.4 |
| 0.20 | 1.5 | 168.2 | 25,230 | 85.4 |
| 0.50 | 1.5 | 175.6 | 26,340 | 89.2 |
| 1.00 | 1.5 | 182.2 | 27,330 | 92.6 |

In absence of salt, 28.1% of the starting activity was solubilized. At the lowest salt concentration, 0.05M, 80% of the activity was recovered as soluble enzyme with a potency of 157.4 IGIU/ml of almost four times that of the starting enzyme extract. Thus, the cation exchange resin greatly enhances the solubilization of isomerase, probably by preferentially adsorbing the quaternary amine from the amine-isomerase complex. In this case the need for higher salt concentration to dissociate the complex is minimized.

EXAMPLE II

This example demonstrates the use of cation exchange resin to preferentially adsorb the quaternary amine in a process wherein the filtration and washing of the amine isomerase precipitate is unnecessary.

A 500 ml portion of the isomerase extract described in the previous example was mixed with 1.0 g Maquat MC 1412—50%. The slurry was stirred for one minute and allowed to settle by gravity. After 60 minutes of settling, 400 ml of clear supernate was carefully removed by siphon and assayed for soluble isomerase activity. This fraction contained only 1.15 IGIU/ml for a total of 460 IGIU or about 2% of the starting activity.

The remaining slurry containing precipitate (about 100 ml) was diluted with 250 ml of water, stirred for about one minute and allowed to settle. After 60 minutes of settling, a total of 260 ml of clear supernate was removed by siphon. This fraction contained less than 100 IGIU isomerase activity.

To the slurry containing precipitate (about 90 ml) was added 90 ml of water, 20 ml of 0.5M NaCl (to make 0.05M NaCl), and 1.4 g d.b. AG50-W-X4 resin. The resulting slurry was divided into equal portions and stirred for either one hour or two hours. The slurries were then filtered and the filtrates were analyzed for soluble isomerase activity. Total recovery of activity in the one hour and two hour filtrates was 20,370 IGIU or 96.5% of the starting activity with an average potency of 77.2 IGIU/ml. There was no significant difference between one hour and two hour solubilizations.

The solubilized enzyme could be adsorbed to DEAE-cellulose at a level of 1970 IGIU/g as compared to a level of 971 IGIU/g for that of the starting extract.

EXAMPLE III

This example demonstrates the use of centrifugation to collect the amine-isomerase precipitate for resolubilization with resin in a minimum volume to prepare a concentrated enzyme extract.

A 1000 ml portion of enzyme extract was treated with Maquat as described in the previous two examples. The precipitate was allowed to settle for two hours and 800 ml of clear supernate was removed by decantation. The remaining 200 ml of slurry was transferred to a 250 ml centrifuge bottle and centrifuged briefly at 8000 rpm using a Sorval RC-2B centrifuge equipped with a GSA rotor. The supernate was decanted and discarded. The precipitate, 7.66 g f.b., was resuspended in 80 ml of 0.05M NaCl and 2.0 g AG50 resin was added. The suspension was stirred for one hour and filtered. The filtrate contained a total of 37,930 IGIU at a potency of 436 IGIU/ml. Thus, the recovery was 92.4% of the starting activity (corrected for sampling losses) and the enzyme concentration was increased more then ten fold when compared to the original extract. The solubilized enzyme could also be adsorbed to DEAE-cellulose at a level of 2070 I.G.I.U./g as compared to a level of 971 IGIU/g for that of the starting extract.

EXAMPLE IV

This example shows the effect of different cation exchange resins on resolubilization of the quaternary amine-isomerase complex.

Four separate 1000 ml portions of Streptomyces cell-free extract (isomerase activity 35.7 IGIU/ml) were adjusted to pH 7.2. To each portion was added 2 g of Maquat MC 1412—50%, and the resulting slurries were stirred 20 minutes at room temperature. The precipitates were allowed to settle by gravity for two hours before decanting 800 ml of each clear supernate. The supernates contained less than 0.2 IGIU/ml indicating that most of the isomerase had been precipitated by the quaternary amine.

The remaining 200 ml of each slurry was centrifuged as in Example III. The supernates were decanted and discarded. Each precipitate was resuspended in 120 ml of 0.05M NaCl, and 2.0 g d.b. portions of various resins were added. The resulting suspensions were stirred for two hours and filtered. Each filter cake was washed with additional 0.05M NaCl, the washings were combined with the filtrates such that the total volume of each was 200 ml, and samples of each were taken for isomerase assay and protein determination. The results are shown in the following table.

| Trial | Resin | Soluble Activity | | Specific Activity | Recovery |
|---|---|---|---|---|---|
| | | IGIU/ml | IGIU/Total | IGIU/mg | % |
| Control | None | 0.73 | 146 | 4.7 | 0.41 |
| 1 | AG-50 | 155 | 31,000 | 12.85 | 85.83 |
| 2 | Duolite C-3 | 159 | 31,800 | 13.30 | 89.08 |
| 3 | Sephadex SP-C-25 | 158 | 31,600 | 15.15 | 88.52 |

Both Duolite C-3, a phenolic macroporous strong acid cation exchange resin (sodium form), and Sephadex SP-C-25, a sulfoethyl derivative of crosslinked dextran (Pharmacia Fine Chemicals) were as effective as the AG-50 resin in solubilizing the quaternary amine-isomerase complex.

What is claimed is:

1. A process for resolubilizing glucose isomerase from an insoluble glucose isomerase-amine complex comprising reacting said complex in an aqueous medium comprising a cation exchange resin.

2. The process according to claim 1 wherein said resin is selected from the group consisting of a polystyrene sulfonic acid resin, a phenolic sulfonic acid resin, and a dextran sulfonic acid resin.

3. The process according to claim 1 wherein said amine is of the formula

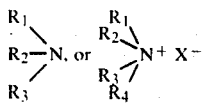

wherein
- $R_1$ is a hydrocarbyl radical of at least 6 carbon atoms;
- $R_2$ is a hydrocarbyl radical of from about 8 to about 20 carbon atoms;
- $R_3$ is lower alkyl;
- $R_4$ is H or lower alkyl; and
- X is an anion.

4. A process according to claim 3 wherein said amine is n-alkyldimethylbenzylammonium chloride.

5. A process for resolubilizing glucose isomerase from an insoluble glucose amine complex comprising reacting said complex in an aqueous medium comprising a cation exchange resin and an ionic salt.

6. The process according to claim 5 wherein said resin is selected from the group consisting of a polystyrene sulfonic acid resin, a phenolic sulfonic acid resin, and a dextran sulfonic acid resin.

7. The process according to claim 5 wherein said amine is of the formula

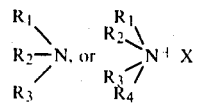

wherein
- $R_1$ is a hydrocarbyl radical of at least 6 carbon atoms;
- $R_2$ is a hydrocarbyl radical of from about 8 to about 20 carbon atoms;
- $R_3$ is lower alkyl;
- $R_4$ is H or lower alkyl; and
- X is an anion.

8. The process according to claim 7 wherein said amine is n-alkyldimethylbenzylammonium chloride.

9. The process according to claim 5 wherein said ionic salt is selected from a group consisting of NaCl, $Na_2SO_4$, KCl, $K_2SO_4$, $KNO_3$, $NaNO_3$, $NH_4Cl$, $(NH_4)_2SO_4$ magnesium salts, manganese salts, cobalt salts, acetate, citrate, maleate, and pyridinium chloride.

10. The process according to claim 9 wherein said salt is NaCl.

* * * * *